(12) United States Patent
Dale (10) Patent No.: US 7,915,017 B2
(45) Date of Patent: Mar. 29, 2011

(54) PROCESS FOR THE TREATMENT OF LIGNOCELLULOSIC BIOMASS

(75) Inventor: Bruce Dale, Mason, MI (US)

(73) Assignee: Board of Trustees of MICHIGAN STATE UNIVERSITY, East Lansing, MI (US)

( * ) Notice: Subject to any disclaimer, the term of this patent is extended or adjusted under 35 U.S.C. 154(b) by 671 days.

(21) Appl. No.: 11/901,336

(22) Filed: Sep. 17, 2007

(65) Prior Publication Data

US 2008/0008783 A1 Jan. 10, 2008

Related U.S. Application Data

(63) Continuation-in-part of application No. PCT/US2007/010415, filed on Apr. 30, 2007.

(60) Provisional application No. 60/796,375, filed on May 1, 2006.

(51) Int. Cl.
*C12P 19/02* (2006.01)
*C12P 7/10* (2006.01)
*C01C 1/00* (2006.01)

(52) U.S. Cl. ........ 435/105; 435/100; 435/101; 435/165; 435/277; 426/69; 127/37; 422/148

(58) Field of Classification Search .................. None
See application file for complete search history.

(56) References Cited

U.S. PATENT DOCUMENTS

| | | | |
|---|---|---|---|
| 4,600,590 | A | 7/1986 | Dale |
| 4,644,060 | A | 2/1987 | Chou |
| 5,037,663 | A | 8/1991 | Dale |
| 5,171,592 | A | 12/1992 | Holtzapple et al. |
| 5,473,061 | A | 12/1995 | Bredereck et al. |
| 5,865,898 | A | 2/1999 | Holtzapple et al. |
| 5,939,544 | A | 8/1999 | Karsents et al. |
| 6,106,888 | A | 8/2000 | Dale et al. |
| 6,176,176 | B1 | 1/2001 | Dale et al. |
| 6,416,621 | B1 | 7/2002 | Karstens |
| 6,444,437 | B1 | 9/2002 | Sporleder et al. |
| 2003/0044951 | A1 | 3/2003 | Sporleder et al. |
| 2007/0031918 | A1 | 2/2007 | Dunson |

FOREIGN PATENT DOCUMENTS

| | | |
|---|---|---|
| DE | 203 01 645 | 4/2003 |
| EP | 1 247 781 | 10/2002 |
| WO | WO 2007/130337 A1 | 11/2007 |

OTHER PUBLICATIONS

Mosier et al "Features of promising technologies for pretreatment of lignocellulosic biomass" online availabiltiy Sep. 2004 Bioresource Tech 96 (2005) 673-686.*
Felix, A., et al., Anim. Prod. 51 47-61 (1990).
Waiss, A.C., Jr., et al., Journal of Animal Science 35 No. 1, 109-112 (1972).
Alizadeh, H., F. Teymouri, T.I. Gilbert, B.E. Dale, 2005. Pretreatment of Switchgrass by Ammonia Fiber Explosion. Applied Biochemistry and Biotechnology, 121-124:1133-1141.
Kudra, T., A.S. Mujumdar, 2002. Advanced Drying Technologies, New York, NY: Marcel Dekker, Inc.
Eggeman, T. 2001. Ammonia Fiber Explosion Pretreatment for Bioethanol Production, National Renewable Energy Laboratory (NREL) Subcontract No. LCO-1-31055-01.
Teymouri, F. et al: "Optimization of the Ammonia Fiber Explosion (AFEX) Treatment Parameters for Enzymatic Hydrolysis of Corn Stover", Bioresource Technology, Elsevier BV, Biotech. 2005.01.016, vol. 96, No. 18, Dec. 1, 2005, pp. 2014-2018.
Supplementary European Search Report for European Patent Application No. 07 77 6479, dated May 26, 2010.
PCT Search Report on Patentability for PCT/US2007/010415, Pub Date Oct. 11, 2007.

* cited by examiner

*Primary Examiner* — Herbert J. Lilling
(74) *Attorney, Agent, or Firm* — Ian C. McLeod; Steven M. Parks (57) ABSTRACT

A process for the treatment of biomass to render structural carbohydrates more accessible and/or digestible using concentrated ammonium hydroxide with or without anhydrous ammonia addition, is described. The process preferably uses steam to strip ammonia from the biomass for recycling. The process yields of monosaccharides from the structural carbohydrates are good, particularly as measured by the enzymatic hydrolysis of the structural carbohydrates. The monosaccharides are used as animal feeds and energy sources for ethanol production.

15 Claims, 6 Drawing Sheets

(4 of 6 Drawing Sheet(s) Filed in Color)

PRIOR ART

PROCESS FOR THE TREATMENT OF LIGNOCELLULOSIC BIOMASS

CROSS-REFERENCE TO RELATED APPLICATIONS

This application is a continuation-in-part of PCT/US07/10415, filed Apr. 30, 2007, designating the U.S., which is based upon Provisional Application Ser. No. 60/796,375, filed May 1, 2006, which are incorporated herein by reference in their entirety.

STATEMENT REGARDING FEDERALLY SPONSORED RESEARCH OR DEVELOPMENT

Not Applicable.

STATEMENT REGARDING GOVERNMENT RIGHTS

Not Applicable.

BACKGROUND OF THE INVENTION (1) Field of the Invention

The present invention relates to a process for the treatment of a lignocellulosic biomass with uniquely effective combinations of water and/or heat and/or anhydrous ammonia and/or concentrated ammonium hydroxide and/or ammonia gas to increase the reactivity of structural carbohydrates (cellulose and hemicellulose) in the biomass. The treatment occurs under greater than ambient pressure. The invention also relates to means whereby ammonia can be maintained in effective contact with the biomass by managing the head space (gaseous phase) of the reactor in which ammonia, biomass and water coexist. In particular, the present invention relates to a process which enables the efficient conversion of structural polysaccharides to valuable products via enzymatic hydrolysis, chemical catalytic conversion, or by direct action of microorganisms, either in human-engineered systems or natural systems such as the animal rumen.

(2) Description of the Related Art

A wide variety of methods (e.g. concentrated or dilute acids or bases, high temperatures, radiation of various forms) have been used to pretreat lignocellulosic biomass to extract structural carbohydrates to be used to obtain monosaccharides for many different uses. The goal of these pretreatments is to increase the rate and/or yield at which the monosaccharides are subsequently obtained from the structural carbohydrates by chemical or biochemical means such as acid catalysis, enzymatic catalysis, fermentation or animal digestion. In general, these pretreatments have fallen short of desired economic and technical performance for several reasons: 1) many pretreatments degrade some of the sugars, e.g. to acids or aldehydes, thus reducing yields and inhibiting subsequent biological conversion of the remaining sugars; 2) when chemicals are used in the pretreatment, it is frequently difficult to recover these chemicals at reasonable cost; 3) residual chemicals can negatively affect downstream conversion operations; and 4) the effectiveness of many pretreatments is limited so that the ultimate conversions of structural carbohydrates obtained, independent of lost yield by sugar degradation reactions, is inadequate for competitive process economics. Thus, there are many prior art methods, and they have numerous drawbacks including those outlined above.

Sufficiently inexpensive monosaccharides from renewable plant biomass can become the basis of chemical and fuels industries, replacing or substituting for petroleum and other fossil feedstocks. Highly reactive lignocellulosic biomass can also become the basis of improved animal feeds, particularly for ruminant animals. Effective, economical pretreatments are required to make these monosaccharides available at high yield and acceptable cost.

The prior art in the pretreatment of plant biomass with anhydrous liquid ammonia or ammonium hydroxide solutions is extensive. Illustrative are the following patents and literature references:

U.S. Pat. No. 4,600,590 to Dale
U.S. Pat. No. 4,644,060 to Chou
U.S. Pat. No. 5,037,663 to Dale
U.S. Pat. No. 5,171,592 to Holtzapple et al.
U.S. Pat. No. 5,865,898 to Holtzapple et al.
U.S. Pat. No. 5,939,544 to Karsents et al.
U.S. Pat. No. 5,473,061 to Bredereck et al.
U.S. Pat. No. 6,416,621 to Karstens
U.S. Pat. No. 6,106,888 to Dale et al.
U.S. Pat. No. 6,176,176 to Dale et al.
U.S. Patent Application No. 2007/0031918, filed Apr. 12, 2006.
Felix, A., et al., Anim. Prod. 51 47-61 (1990)
Waiss, A. C., Jr., et al., Journal of Animal Science 35 No. 1, 109-112 (1972). All of these patents and publications are incorporated herein in their entireties.

In particular, ammonia fiber explosion (AFEX) represents a unique and effective pretreatment for biologically converting lignocellulosic biomass to ethanol (Dale, B. E., 1986. U.S. Pat. No. 5,037,663; Dale, B. E., 1991. U.S. Pat. No. 4,600,590; Alizadeh, H., F. Teymouri, T. I. Gilbert, B. E. Dale, 2005. Pretreatment of Switchgrass by Ammonia Fiber Explosion. Applied Biochemistry and Biotechnology, 121-124: 1133-1141; Dale, B. E., 1991. U.S. Pat. No. 4,600,590; Dale, B. E., 1986. U.S. Pat. No. 5,037,663). In AFEX pretreatment, lignocellulosic biomass is exposed to concentrated ammonia at elevated pressures sufficient to maintain ammonia in liquid phase and moderate temperatures (e.g. around 100° C.). Residence times in the AFEX reactor are generally less than 30 minutes. To terminate the AFEX reaction, the pretreated biomass is depressurized (flashed). The AFEX process is not and has never been limited to the application of anhydrous ammonia with AFEX. Some water is always initially present with the biomass and sometimes water is added to the biomass, so that any anhydrous ammonia is immediately converted into a concentrated ammonia water mixture on beginning the AFEX treatment. However, a detailed exploration of how ammonia and water are best combined with each other and with the biomass to achieve effective pretreatment has never been performed.

Figure 1:
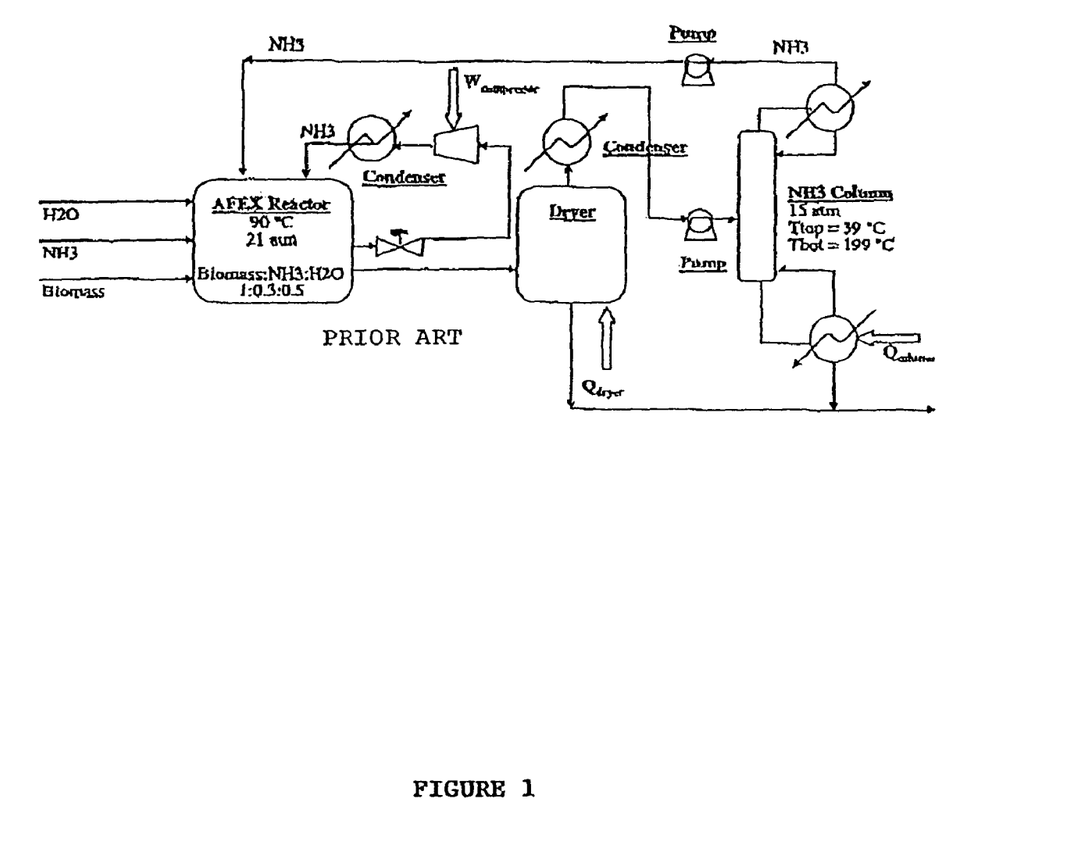
FIG. 1 is a process flow diagram for a prior art AFEX pretreatment with ammonia recovery and recycling.

Recovery of ammonia used in AFEX pretreatment is a key objective when integrating AFEX into a broader biomass conversion process design. The existing ammonia recovery design (Eggeman, T. 2001. Ammonia Fiber Explosion Pretreatment for Bioethanol Production, National Renewable Energy Laboratory (NREL) Subcontract No. LCO-1-31055-01), which is depicted in FIG. 1, calls for compressing ammonia, which is vaporized as a result of the flash operation, and separating ammonia that remains in contact with the pretreated solids via evaporation in a dryer. The resulting vapor, which also contains water, is then delivered to a distillation column to concentrate the ammonia. The ammonia from the column is pumped up to pressure and, together with the compressed flash ammonia, is recycled to the AFEX reactor. FIG. 1 shows the existing ammonia recovery approach.

FIG. 1 shows the prior art system 10 including a closed AFEX reactor vessel 12 into which biomass, water and ammonia are introduced under pressure. Valve $V_1$ is used to release pressure from the vessel 12. The treated biomass is transferred to a heated dryer 14. The dried biomass is transferred out of the dryer 14 for subsequent treatment. Ammonia from the dryer 14 is condensed by condenser 22 and sent to slurry column 16. Water is removed and condensed by condenser 18. Ammonia is condensed in condenser 20 and recycled to the vessel 12. Ammonia gas is pressurized in a compressor 24, condensed and recycled into vessel 12. It is obvious to one skilled in the art that the ammonia pretreatment and recovery processes generate ammonia and water mixtures of differing phases (gaseous and liquid), compositions and temperatures. These resulting ammonia and water mixtures can therefore potentially be combined with each other and with new biomass to be treated in many different compositions and phases (gas and liquid).

The problem is that some of these potential ammonia and water treatment processes may either produce relatively low biomass reactivity and/or may require large amounts of liquid ammonia or ammonium hydroxide solutions. The most effective approaches to combine recycled ammonia and water of different compositions and phases to produce a highly reactive biomass are not well-understood. The optimal order of addition of water, ammonia and ammonia-water mixtures, and their relative amounts, temperatures and concentrations, has not been sufficiently defined so as to produce acceptable biomass reactivity. Furthermore, methods for maintaining ammonia in effective contact with the biomass, so as to reduce the total amount of ammonia required, have not been described.

OBJECTS

It is therefore an object of the present invention to provide a process by which ammonia, water and biomass are combined in uniquely effective ways to produce highly reactive structural polysaccharides within the biomass. The results obtained are novel, unexpected and useful. Further, it is an object of the present invention to provide means by which the ammonia can be maintained in effective contact with the biomass during the treatment process. Further, it is an object of the present invention to provide an economical process which enables the production of monosaccharides in high yield from the structural carbohydrates. These and other objects will become increasingly apparent by reference to the following description and the drawings.

SUMMARY OF THE INVENTION

The present invention provides a process for the treatment of a plant biomass to increase the reactivity of plant polymers, comprising hemicellulose and cellulose, which comprises: contacting the plant biomass, which has been ground and which contains varying moisture contents, with anhydrous ammonia in the liquid or vapor state, and/or concentrated ammonia:water mixtures in the liquid or vapor state, to obtain a mixture in which the ratio of ammonia (as $NH_3$) to dry biomass is between about 0.2 to 1 and 1.2 to 1, and the water to dry biomass ratio is between about 0.2 to 1.0 and 1.5 to 1, maintaining the mixture in a closed vessel at temperatures between about 50° C. and 140° C. for a period of time; rapidly releasing the pressure by releasing ammonia from the vessel to form a treated biomass; removing the treated plant biomass which has increased reactivity from the vessel. Preferably, the treated biomass is hydrolyzed with enzymes to produce sugars. Preferably, the treated biomass is extracted to remove lignin and other compounds that can interfere with the ability of enzymes to hydrolyze the treated biomass. Preferably, the treated biomass is extracted to remove lignin and other compounds that can interfere with the ability of microorganisms to ferment the treated biomass. Preferably, the ammonia is compressed by a mechanical means for reducing the volume in a headspace inside the closed vessel and thereby increasing the fraction of the total ammonia that is in the liquid phase. Preferably, nitrogen under pressure is introduced into a headspace of the vessel so as to increase the fraction of the total ammonia that is in the liquid phase. Preferably, particles of an inert solid material are introduced into the vessel so as to increase the fraction of the total ammonia that is in the liquid phase. Preferably, particles of a solid material selected from the group consisting of sand and iron filings are introduced into the vessel so as to increase the fraction of the total ammonia that is in the liquid phase. Preferably, the headspace (gas phase) of the reactor vessel is connected with the headspace of an appropriate ammonia storage vessel so as to increase the fraction of the total ammonia that is in the liquid phase. Preferably, the treated biomass is hydrolyzed with enzymes to produce sugars and wherein the sugars are fermented by a microorganism to produce a fermentation product. Preferably, the treated biomass is fermented by a microorganism to produce a fermentation product without a separate sugar production step. Preferably, the treated biomass containing more digestible plant polymers is consumed by an animal. Preferably, the plant biomass is fermented to produce ethanol.

One skilled in the art will realize that within a facility pretreating biomass containing some water with ammonia and perhaps adding more water, heating the mixture, allowing the hot ammonia:water:biomass combination to react for a time, ending the reaction by removing the ammonia from biomass, and separating ammonia from water in the recovery process, a variety of possible ammonia:water:biomass combinations present themselves. Some combinations may prove more technically and/or economically effective than others in producing a highly reactive biomass. The present invention relates to effective treatments of a plant biomass to increase the reactivity of plant structural carbohydrates. The results are novel, unexpected and useful. At the same final conditions (temperature, amount of total water, ammonia and biomass mixed with each other), uniquely effective combinations of ammonia, water and biomass are available. Other combinations giving the same final conditions are much less effective in producing a highly reactive biomass.

For example, Table 1 shows the results of enzymatic hydrolysis of biomass treated with ammonia, water and heat under the same final conditions of 1 kg of ammonia per 1 kg of corn stover biomass (dry weight) and 0.6 kg of water per kg of corn stover biomass (dry weight) at a final reaction temperature of 90 C. These final conditions were chosen to reproduce the optimal pretreatment conditions demonstrated for "conventional" (using anhydrous ammonia) AFEX treatment of corn stover. The first row of results shows the glucose and xylose yields (92.96% and 74.75%, respectively) obtained under these "conventional" AFEX pretreatment conditions. As stated above, it is apparent to one skilled in the art, that different combinations of ammonia, water and biomass will be available, or could readily become available, in a pretreatment facility. The question is: "which combinations of these are most effective in producing a highly reactive pretreated biomass". Experiments 1-15 provide a preliminary answer to this critically important question.

Final glucose yield, and to a lesser extent, xylose yield, following enzymatic hydrolysis are key determinants of process economics for biomass conversion systems. If 90% yield of glucose is somewhat arbitrarily chosen as the target economic yield, then it becomes obvious that only a fraction of all of the possible means for reaching the desired final conditions of 1:1 ammonia to biomass and 0.6:1 water to biomass are in fact effective in achieving this target yield. For example, from Table 1, experiments #6 and #9 differ only in the amount of water that is added to the system via biomass or via ammonium hydroxide, and yet the differences in enzymatic hydrolysis yields are huge, 58% vs. 99%, respectively. These results are unexpected, novel and useful. It is not apparent at all why combining ammonia, water and biomass in different initial proportions but the same final proportions should achieve such different results, but in fact, this is what happens. It is a novel result that has never before been reported, to the inventor's knowledge. Finally, it is an extremely useful result because the operator of the pretreatment facility now has available different routes to achieving an effective pretreatment. Some of these sets of effective conditions may prove much easier or less expensive to implement in an operating pretreatment facility, and hence will be preferred.

Figure 3:
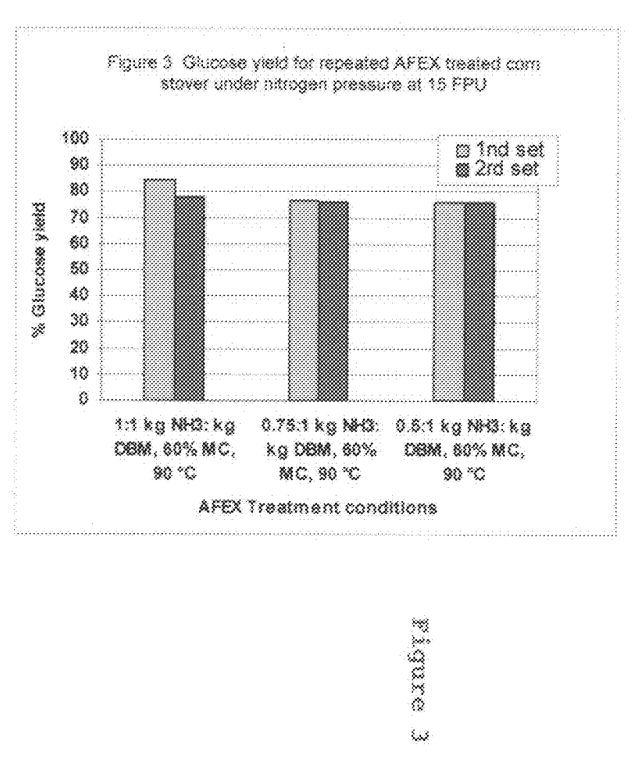
FIG. 3 is a graph showing glucose yield from AFEX treated corn stover experiments under nitrogen pressure.
Figure 4:
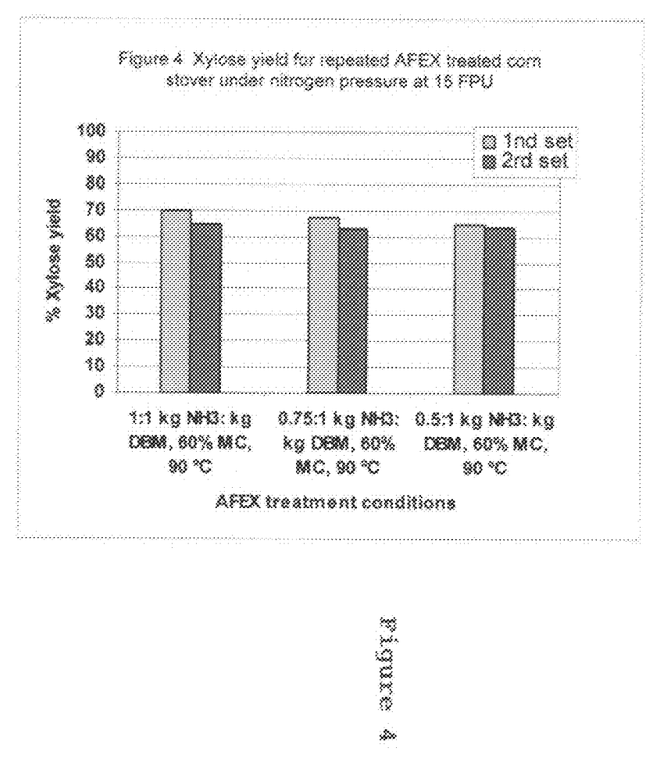
FIG. 4 is a graph showing xylose yield from AFEX treated corn stover experiments under nitrogen pressure.
Figure 5:
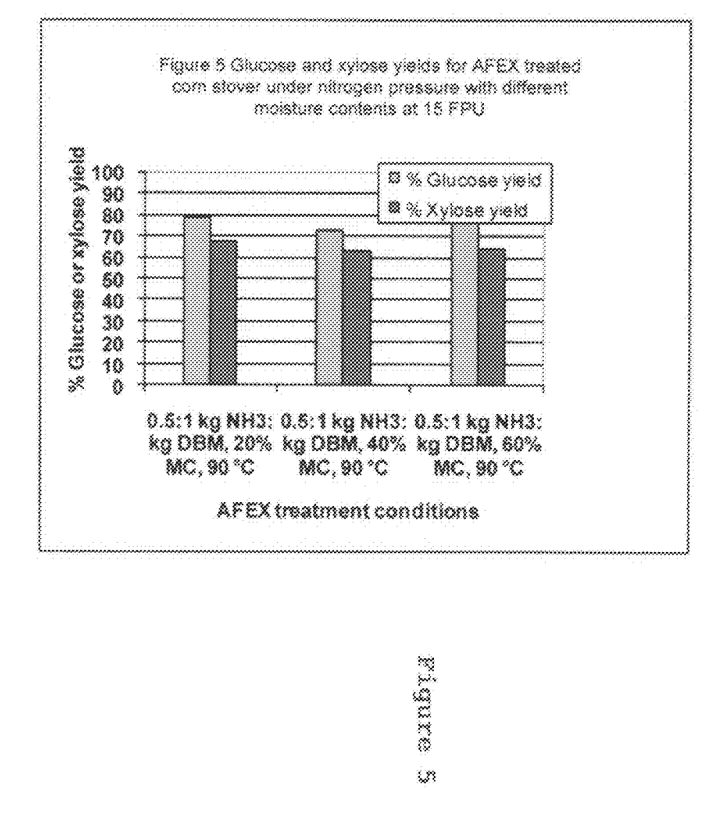
FIG. 5 is a graph showing that while 40% moisture content gives lower yield, 20% biomass moisture content (MC) yields better results a few percent higher than that of 60% MC. The optimal condition has been 60% MC.
Figure 6:
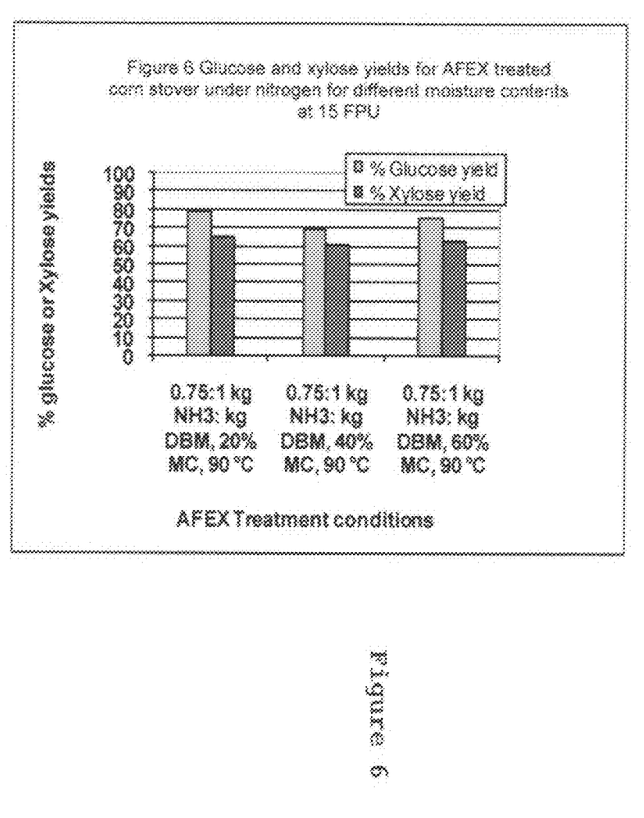
FIG. 6 is a graph showing a similar trend for different sets of experiments with different ammonia loadings. Lower amount of moisture content, i.e. 20% gives a better result.
Figure 7:
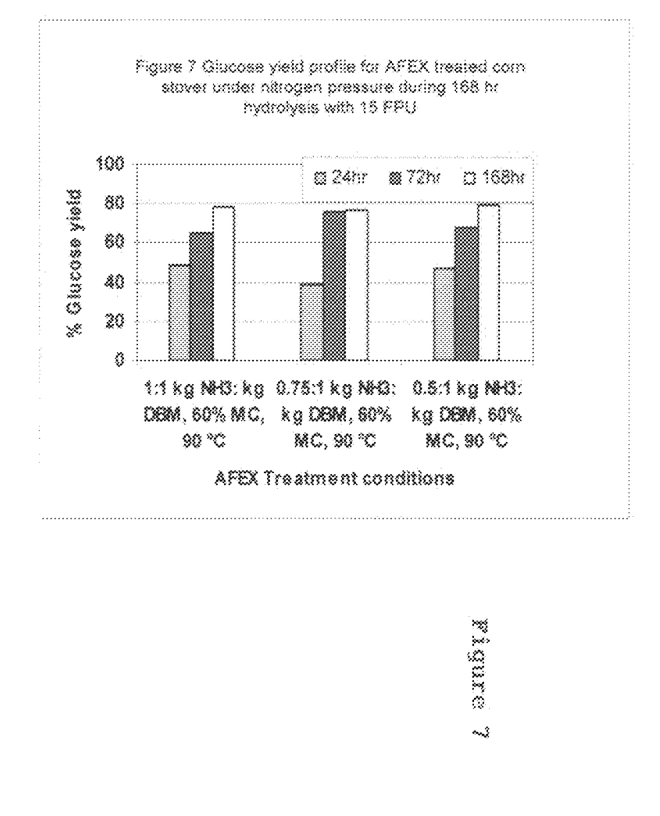
FIG. 7 is a graph showing the glucose profile during 168 hr hydrolysis for different amounts of ammonia loading.
Figure 8:
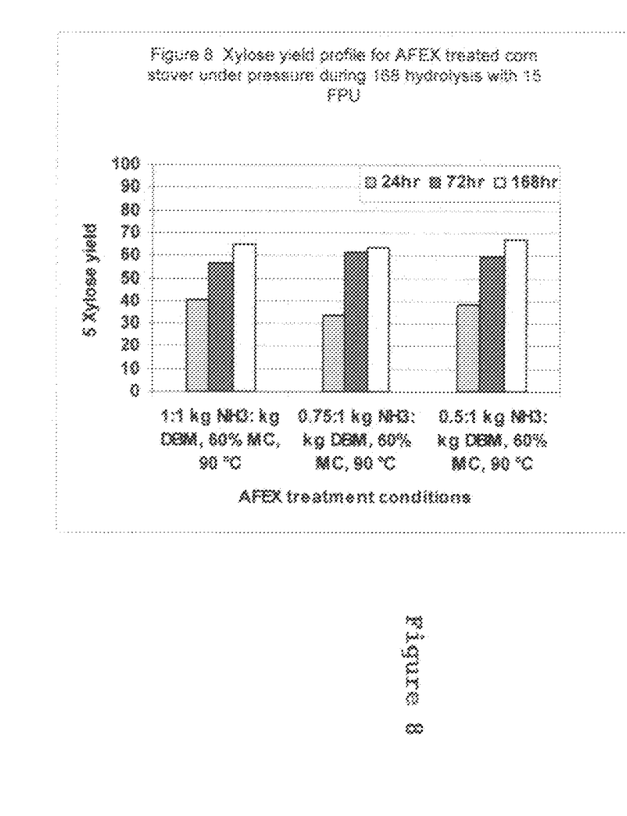
FIG. 8 is a graph showing the xylose profile during 168 hr hydrolysis for different amounts of ammonia loading.
Figure 9:
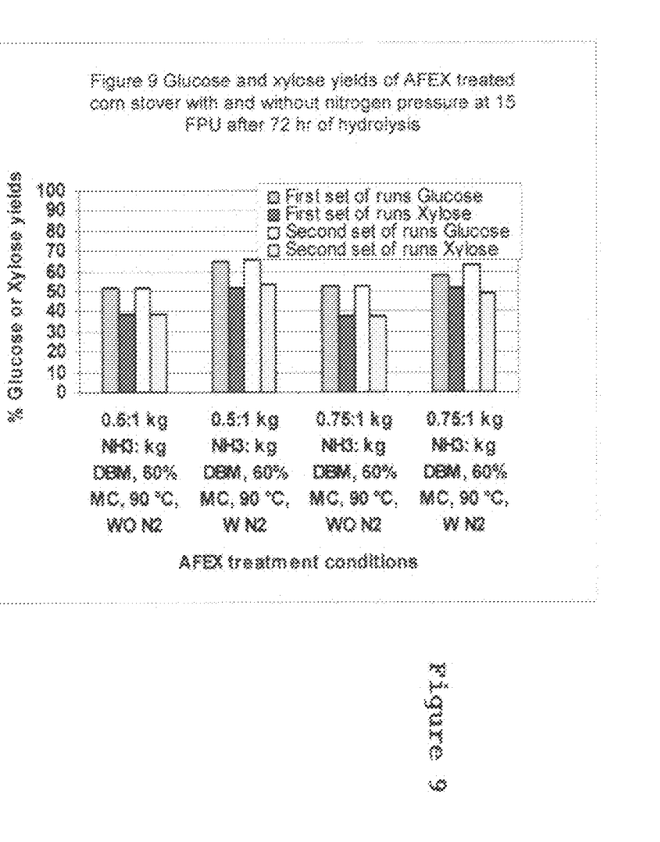
FIG. 9 is a graph showing the overall glucose and xylose yields of two separate sets of AFEX treated corn stover under nitrogen pressure that are repeated. All the runs have yielded very similar results. While higher yield is obtained under nitrogen pressure, a better yield is obtained with 0.5 kg $NH_3$:1 kg DBM, 60% MC under nitrogen pressure.
Figure 10:
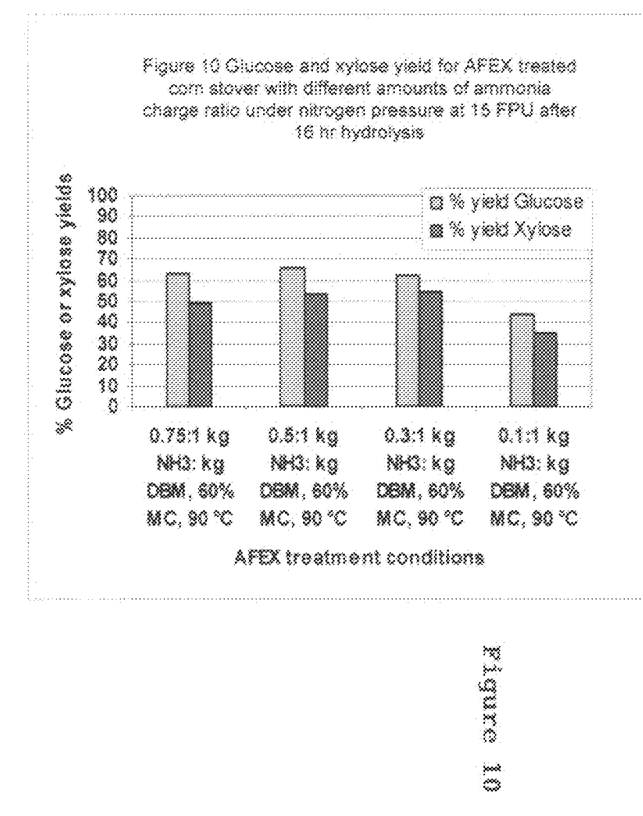
FIG. 10 is a graph showing the yield trend as the kg amount of ammonia per unit kg of dry biomass (DBM) is decreased.

One skilled in the art will also recognize that it is necessary to maintain ammonia and water in effective contact with the biomass during the pretreatment process. The present invention also provides means for maintaining ammonia and water in contact with the heated mixture by minimizing or otherwise managing the headspace (vapor phase) of the reactor containing heated biomass, ammonia and water. Various approaches can be envisioned to achieve this objective. Preferably, the ammonia in step (b) is compressed by a mechanical means for reducing the volume of a headspace inside the closed vessel and thereby increasing a fraction of the total ammonia that is in the liquid phase. Preferably, nitrogen or another inert gas under pressure is introduced into a headspace of the vessel in step (b) so as to increase a fraction of the total ammonia that is in the liquid phase. Preferably, particles of an inert solid material are introduced into the vessel so as to increase a fraction of the total ammonia that is in the liquid phase. Preferably, particles of a solid material selected from the group consisting of sand and iron filings are introduced into the vessel so as to increase a fraction of the total ammonia that is in the liquid phase. FIGS. 3 and 4 show that by maintaining nitrogen pressure on the headspace of the reactor, the amount of ammonia required to obtain a desired glucose yield can be reduced. Nitrogen overpressure minimizes the amount of ammonia that evaporates from the biomass and keeps more ammonia in contact with the biomass, thereby increasing treatment effectiveness. This is strong support for the idea that minimizing ammonia in the gas phase will maximize treatment effectiveness. Obviously, other means of minimizing gas phase ammonia are available. These include combining inert solids (e.g., sand or iron filings) or simply connecting the headspace of the reactor with the headspace of a storage vessel containing ammonia and water that provides the same gas phase composition of ammonia and water as is produced under the desired reactor conditions of temperature, ammonia and water levels.

The substance and advantages of the present invention will become increasingly apparent by reference to the following drawings and the description.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 3 and 4 together show that two separate AFEX treated corn stover experiments under nitrogen pressure with the same treatment conditions have similar yields.

While both FIGS. 7 and 8 show similar hydrolysis rates, 0.75 kg $NH_3$:1 kg DBM is favored.

DESCRIPTION OF THE PREFERRED EMBODIMENTS

Cellulosic biomass contains large amounts of structural carbohydrates or polysaccharides (cellulose, hemicellulose, and the like) that can provide much less expensive simple sugars for fermentation or non-biological transformation to a variety of products or as improved animal feeds. However, these polysaccharides are difficult to access. The present invention provides pretreatment process using concentrated ammonium hydroxide under pressure to improve the accessibility/digestibility of the polysaccharides from a cellulosic biomass. The present invention preferably uses combinations of anhydrous ammonia and concentrated ammonium hydroxide solutions to obtain results that are not obtained by either dilute ammonium hydroxide or anhydrous ammonia acting alone. This invention also uses various approaches to minimize the amount of ammonia in the gas phase so that the maximum amount of ammonia is always in the liquid phase and is available to react with the biomass, either as ammonium hydroxide or liquid ammonia.

In the present invention, the lignocellulosic material is treated with concentrated ammonium hydroxide in an amount greater than 30% by weight in an ammonium hydroxide solution. The process can be performed in a continuous reactor or a batch reactor as in the Examples.

The biomass contains water which is naturally present. Typically, this natural water represents about 1% to 20% by weight of the biomass. In general, this natural water tends to be bound in the biomass and thus the water which is primarily relied upon is that added with the ammonium hydroxide solution. Water can also be added to the biomass and, if so, then this mixes with the ammonium hydroxide to provide the ammonium hydroxide solution. Up to 50% of the biomass can be added water.

The term "lignocellulosic biomass" means a naturally derived lignin and cellulose based material. Such materials are, for instance, alfalfa, wheat straw, corn stover, wood fibers, and the like. Preferably the materials are comminuted into particles in a longest dimension.

The term "structural carbohydrates" means the polysaccharide materials containing monosaccharide moieties available by hydrolysis.

The mass ratio of a lignocellulose biomass to ammonia is preferably 1 to 1; however, the mass ratio can be between 0.3 and 1.2 to 1.0.

The reaction temperature is preferably 90° C.; however, the temperature can be between 50° C. and 120° C.

The pressure is preferably between 100 psi and 300 psi (6.9 to 20.7 atm); however, pressures between 4 and 50 atm can be used.

Hot ammonium hydroxide/water solutions or hot ammonia/water vapors can be added to ground lignocellulosic biomass in a contained vessel to obtain final mixture temperatures of 50° C. or above, preferably 90° C. A preferred ammonia to dry biomass mass weight ratio was about 0.2 to 1.2. A preferred water to dry biomass mass ratio was about 0.4 to 1.0.

Figure 2:
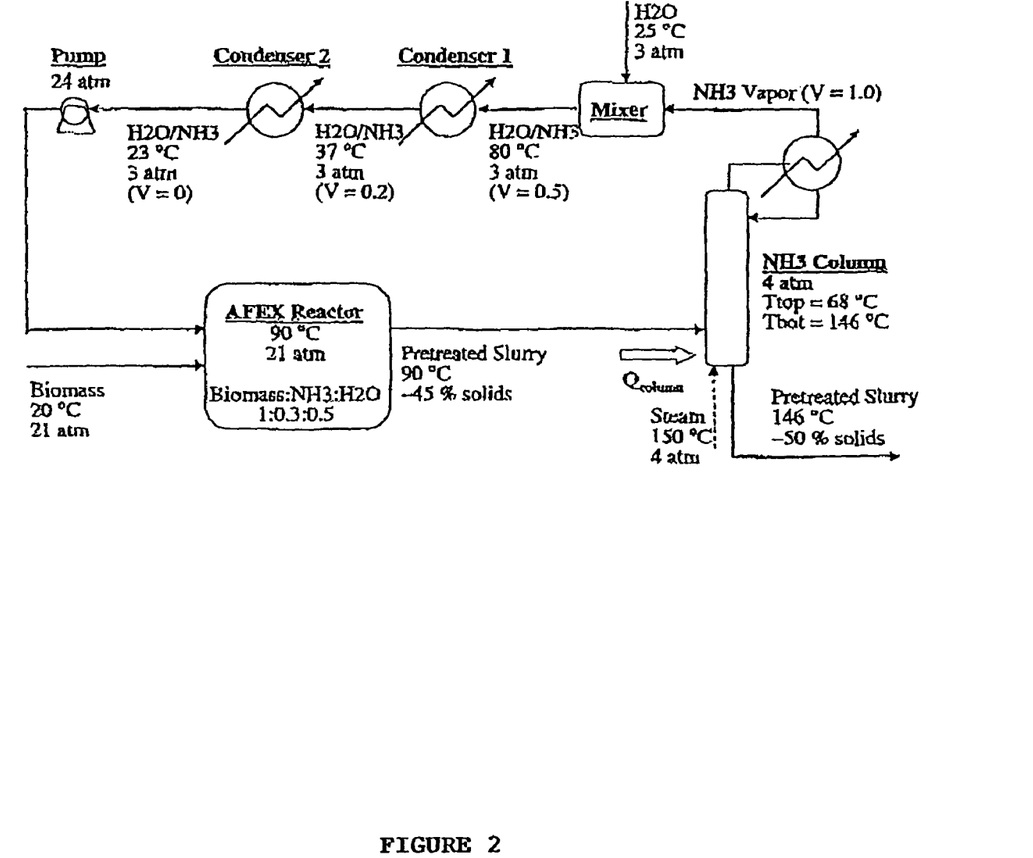
FIG. 2 is a process flow diagram for the present invention for AFEX pretreatment with an efficient ammonia recovery.

FIG. 2 shows the improved system 100 with AFEX reactor vessel. The slurry is sent directly to the stripping column 104 and condenser in condenser 106 and is sent to mixer 108 for addition of water. High pressure steam is used in the stripping column 104 to remove the ammonia from the slurry. The hot aqueous slurry is removed from the bottom of the stripping column. Condensers 110 and 112 are used to cool the water and ammonia mixture which is recycled into the vessel 102. By comparing FIGS. 1 and 2, it can be seen that the process of FIG. 2 is more efficient.

EXAMPLES 1 TO 20

A 300 ml pressure vessel 102 was first filled with a given mass of corn stover wetted to the desired moisture level as indicated in Table 1 and the vessel 102 was sealed. Then a concentrated ammonium hydroxide mixture was prepared by mixing the right proportions of anhydrous ammonia and water in another pressure vessel and this mixture was added to the corn stover in the 300 ml reactor vessel 102 to achieve the desired final level of ammonia and water. In this case, the target was 1 kg of ammonia per kg and dry biomass and 0.6 kg of water per kg of dry biomass. The mixture of ammonia, water and biomass was then heated to 90° C., held at that temperature for 5 minutes and the pressure rapidly released.

The resulting solid was hydrolyzed to mixtures of monosaccharides containing, for example, glucose, xylose and arabinose.

The results of the present invention are shown in Table 1 and Examples 2 to 15.

TABLE 1

Glucose and Xylose yields of ammonia treated corn stover after 168 hr (7 days) for hydrolysis with a cellulose enzyme. Different ammonia concentrations were used. All runs are at 1 kg NH3:1 Kg dry stover (BM), 90° C. reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 1 (a) | 1 | All $NH_3$ | All in BM | 92.96 | 74.25 | 2 |
| 2 | 0.5 | ¾ $NH_3$ and ¼ $NH_4OH$ | ½ in $NH_4OH$ ½ in BM | 92.20 | 78.85 | 2 |
| 3 | 0.5 | ¾ $NH_3$ and ¼ $NH_4OH$ | All in $NH_4OH$ | 79.88 | 64.90 | 2 |
| 4 | 0.41 | ⅔ $NH_3$ and ⅓ $NH_4OH$ | All in $NH_4OH$ | 86.60 | 70.54 | 1 |
| 5 | 0.58 | ⅔ $NH_3$ and ⅓ $NH_4OH$ | ½ in $NH_4OH$ ½ in BM | 78.23 | 65.83 | 1 |
| 6 | 0.5 | ½ $NH_3$ and ½ $NH_4OH$ | All in $NH_4OH$ | 57.65 | 47.85 | 1 |
| 7 | 0.8 | ½ $NH_3$ and ½ $NH_4OH$ | ¾ in NH4OH and ¼ in BM | 85.50 | 70.37 | 1 |
| 8 | 0.66 | ½ $NH_3$ and ½ $NH_4OH$ | ½ in $NH_4OH$ ½ in BM | 97.78 | 81.98 | 2 |
| 9 | 0.79 | ½ $NH_3$ and ½ $NH_4OH$ | ¾ in BM and ¼ in $NH_4OH$ | 98.54 | 78.70 | 2 |
| 10 | 0.38 | ⅓ $NH_3$ and ⅔ $NH_4OH$ | All in $NH_4OH$ | 74.52 | 56.47 | 1 |
| 11 | 0.73 | ⅓ $NH_3$ and ⅔ $NH_4OH$ | ½ in $NH_4OH$ ½ in BM | 81.51 | 69.66 | 1 |
| 12 | 0.66 | All $NH_4OH$ | All in $NH_4OH$ | 71.00 | 57.00 | 2 |
| 13 | 0.75 | All $NH_4OH$ | ½ in $NH_4OH$ ½ in BM | 96.78 | 79.00 | 3 |
| 14 | 0.88 | All $NH_4OH$ | ¾ in $NH_4OH$ and ¼ in BM | 97.11 | 79.00 | 2 |
| 15 | 0.72 | All $NH_4OH$ | ¼ in $NH_4OH$ and ¾ in BM | 88.31 | 75.37 | 2 |

TABLE 1-continued

Glucose and Xylose yields of ammonia treated corn stover after 168 hr (7 days) for hydrolysis with a cellulose enzyme. Different ammonia concentrations were used. All runs are at 1 kg NH3:1 Kg dry stover (BM), 90° C. reactor temperature, 0.6 kg water/kg dry stover (except for the last 4 experiments 17 to 20) and 5 min residence time. 15 FPU cellulase enzyme/gram glucan in BM.

| Expt. # | Kg $NH_3$/kg water in ammonium hydroxide | Ammonia distribution | Water distribution | % Glucose yield | % Xylose yield | Repeats |
|---|---|---|---|---|---|---|
| 16 (b) | 0.3 | All $NH_4OH$ | 2.3 g water per g BM | 83.58 | 68.18 | 1 |
| 17 (b) | 0.15 | All $NH_4OH$ | 5.6 g water per g BM | 70.50 | 42.46 | 1 |
| 18 (b) | 0.1 | All $NH_4OH$ | 9 g water per g BM | 64.85 | 49.31 | 1 |
| 19 (b) | 0.05 | All $NH_4OH$ | 19 g water per g BM | 51.26 | 39.32 | 1 |
| 20 (c) | Control | No ammonia | Not applicable | 29.5 | 17.5 | 2 |

Note:
Pressures range from about 100 psi to about 300 psi except for Expt. 16-19, which are at atmospheric pressure
(a) Comparative Example 1 shows the AFEX process described in U.S. Pat. Nos. 4,600,590 and 5,037,663 to Dale, exemplified by FIG. 1.
Comparative Examples 16 to 19 (b) show the results at atmospheric pressure with ammonium hydroxide.
Example 20 (c) shows the process without ammonia.

Table 1 shows the results for the conversion of corn stover to glucose and xylose following treatment with ammonia and water. The total amount of water, ammonia and biomass and the system temperature is the same in all cases. The biomass was treated with 1 kg of ammonia per 1 kg dry corn stover biomass (the untreated stover has a moisture content of about 15% dry basis). The experiments were run at 90° C. with a five minute holding time at that temperature and the treated material of Example 1 was hydrolyzed with 15 filter paper units of cellulose per gram of cellulose in the stover. From the point of view of the final conditions to which the stover was subjected, these conditions are identical. However, the way in which these final conditions were reached was varied significantly and novel, surprising results were obtained.

Columns 3 and 4 of the Table show how this was done. For example, the column titled "Ammonia Distribution" shows whether the ammonia (as NH3) was added as anhydrous ammonia or as ammonium hydroxide (ammonia in water). For example, "all NH3" means that all of the ammonia was added to the biomass as anhydrous liquid ammonia as in Example 1 directly from the pressure tank. "ALL NH4OH" means all of the ammonia was added as aqueous ammonium hydroxide.

The fourth column ("Water Distribution") shows whether the water was added to the stover directly or added as part of the ammonium hydroxide. In the first row for Experiment 1a ("conventional AFEX"), "all NH3" and "All of the water in BM" means that all the ammonia was added as anhydrous and all of the water was in the biomass as in Example 1. The last set of rows is for "All NH4OH" meaning that all of the ammonia was added as ammonium hydroxide and the water was added either to the stover or with the ammonium hydroxide. These rows (Experiments 16-19) represent essentially ambient pressure treatments of biomass by ammonia, not the concentrated ammonia systems at higher than ambient pressure of Experiments 1-15 above.

Thus, depending on how the ammonia and water are added, very different results are obtained. Eighty-five percent (85%) conversion of cellulose to glucose is used as the minimum for a cost competitive process. Using that criterion, the final column shows the % yield after 168 hours of hydrolysis for both glucose (G) and xylose (X). In no case, when all of the water was added as ammonium hydroxide (comparatively more dilute ammonium hydroxide) is the 85% criterion achieved.

The specific features of the process of the present invention that make it more advantageous than prior art methods are as follows: (1) it does not degrade any biomass carbohydrates so that yield is not compromised due to the pretreatment; (2) high overall yields of glucose (nearly 100% of theoretical) and 85% of theoretical yields of xylose, are obtained; (3) low application rates of otherwise expensive hydrolytic enzymes are needed to obtain these yields; (4) residual ammonia can serve as a nitrogen source for subsequent fermentations or animal feeding operations; (5) treated biomass and polysaccharides can be fed at very high solids levels to subsequent process operations, thereby increasing the concentration of all products and reducing the expense of producing other chemicals from the polysaccharides; (6) using different ammonia and ammonium hydroxide combinations, in combination with different water levels in the biomass, fits well into recovery operations for the ammonia and gives the plant operator additional flexibility to minimize costs and maximize treatment effectiveness; and (7) managing the reactor headspace to minimize ammonia evaporation into the gas phase further improves process economics by minimizing the amount of ammonia required to achieve an effective treatment.

Markets that can use this invention include: (1) the U.S. chemical industry which is beginning to move away from petroleum as a source of chemical feedstocks and is interested in inexpensive monosaccharides as platform chemicals for new, sustainable processes; (2) the fermentation industry, especially the fuel ethanol production industry which is also interested in inexpensive sugars from plant biomass; and (3) the animal feed industry which is strongly affected by the cost of available carbohydrates/calories for making animal feeds of various kinds.

The following Example 16 describes two (2) design features that reduce process energy requirements relative to existing designs of ammonia recovery for AFEX pretreatment: (1) steam stripping of pretreated material; and (2) water quench condensation of ammonia vapor. FIG. 2 presents a process flow sheet of these features in the context of the broader AFEX pretreatment design.

Steam Stripping of Pretreated Material

After the AFEX pretreatment is complete, the pretreated material is flashed to a lower pressure, as in the existing design. Unlike the existing design; however, the present invention uses steam-stripping of the resulting pretreated solids to recover residual ammonia. This feature enables the elimination of energy intensive solids drying that is used in the design of FIG. 1. The processing equipment can be similar to that used for direct steam drying of solids for which there are an increasing number of commercial examples (Kudra, T., A. S. Mujumdar, 2002. Advanced Drying Technologies, New York, N.Y.: Marcel Dekker, Inc.; Pronyk, C., S. Cenkowski, 2003. "Superheating Steam Drying Technologies," ASAE Meeting Presentation, Paper Number RRV03-0014.).

Water Quench Condensation of Ammonia Vapor

Ammonia vapor coming from the ammonia recovery steam stripping column is combined with ammonia vapor arising from the post-AFEX flash operation and condensed by first adding water in the mixer and then indirectly cooling the aqueous solution in two steps, first with cooling water, and then with chilled water. The condensed aqueous mixture is then pressurized via liquid pumping and recycled to the AFEX reactor. These steps eliminate the need for ammonia vapor compression that is used in the design of FIG. 1.

Utility of Invention

Based on Aspen Plus (a commercially available modeling software) process simulations of the process of FIGS. 1 and 2, the present invention requires significantly less process energy relative to the existing design, as indicated in Table 2. Furthermore, it is anticipated that the invention will result in lower processing costs as well.

TABLE 2

Comparison of process energy requirements: proposed versus existing design for AFEX pretreatment with ammonia recovery.[1,2]

| Energy Flow | FIG. 1 Design Required Energy (% feedstock LHV) | FIG. 2 Design Required Energy (% feedstock LHV) |
| --- | --- | --- |
| Steam to dryer | 7.73% | — |
| Steam to NH3 column | 2.87% | 3.82% |
| Power to compressor | 0.02% | — |
| Power to chilled water unit | — | 0.14% |
| TOTAL | 10.62% | 3.96% |

[1]Energy necessary to achieve AFEX reaction temperature is met entirely by heat of mixing between ammonia and water in the reactor.
[2]Both designs use the same ammonia and water loadings: 0.3 g NH$_3$/g biomass; 0.5 g H$_2$0/g biomass.

These steps are in general:
1. Add hot ammonium hydroxide/water solutions or hot ammonia/water vapors to ground lignocellulosic biomass in contained environments to obtain final mixture temperatures of 50° C.
2. Obtain intermediate ammonia to dry biomass mass ratio is about 0.2 to 1.0 while water to dry biomass mass ratio is about 0.4 to 1.0.
3. Allow sufficient time for reaction to occur under these conditions, approximately 5 minutes.
4. Compress the ammonia treated biomass, for example in a screw reactor, to minimize the volume of vapor or "dead" space.
5. Further reduce the tendency of ammonia to convert to a gas by, for example, pressurizing the system with an inert gas such as nitrogen, or by mixing finely divided solids such as sand or iron filings with the biomass.
6. Add essentially anhydrous liquid ammonia to the intermediate mixture to obtain a final ammonia level of about 0.5 kg ammonia (as NH3) per kg of dry biomass and temperatures of about 90° C.
7. Hold new mixture at these conditions for an additional 5 minutes.
8. Rapidly release the pressure to remove and recover the ammonia.
9. Hydrolyze the resulting solids to mixtures of simple sugars containing, for example, glucose, xylose and arabinose.

EXAMPLES 21 TO 36

AFEX Treatment of Corn Stover Under Nitrogen Pressure
Objective:
The main objective of these series of experiments was twofold:
1. To establish the fact that the ammonia in the liquid phase where it is in direct contact with the biomass is preferred phase that makes the AFEX an effective pretreatment process. Therefore, to minimize ammonia evaporation, applying nitrogen pressure during pretreatment of biomass is warranted.
2. To optimize the ammonia loading under nitrogen.

Experimental Procedure:

Old corn stover with 36.1% Glucan content was received from NREL (Golden, Colo.). The moisture content of the biomass was adjusted from 10% to the desired level before placing in the reactor. The reactor was a 300 ml PARR unit with pressure and temperature monitoring attachments. The sample in the reactor topped up with some spherical steel balls to reduce the void in the reactor and to have similar conditions with experiments without use of nitrogen.

A predetermined amount of anhydrous ammonia was charged in a reactor using a sample cylinder. Nitrogen gas was introduced to the reactor from a nitrogen cylinder tank via a pressure regulator. The reactor was gradually heated up by a heating mantle until it reached 90° C. After 5 min of residence time, the reactor was depressurized at once. Both T and P was recorded every 2 min during the experiments. The pressure started at about 400 psig and ended at about 750 psig while the reactor temperature started from about 50° C. to 90° C. where it was vented.

Experimental Conditions:

Two sets of Experiments were conducted. For the first 4 Experiments 21 to 24, the previous optimal conditions of 60% dwb biomass moisture content, 90° C. treatment temperature and 5 min residence time was chosen but the amount of charged ammonia was varied to determine optimal ammonia loading under $N_2$ pressure.

For the second set of 6 Experiments 25 to 30, both the moisture content and ammonia loading was varied. Some of the first set of Experiments was repeated in the second set as well. The repeated Experiments showed similar results. A third set of 6 Experiments 31 to 36, was not conclusive for all the runs possibly due to bad hydrolysis.

Hydrolysis:

For Hydrolysis, NREL Lap-009 protocol was followed. Duplicate samples were prepared and hydrolyzed for a period of 168 hr. At time intervals of 24 hr, 72 hr and 168 hr, samples were taken for HPLC analysis. To all samples were added 15 FPU per g of glucan of Spezyme CP (CAFI 1), Old enzyme with 28.2 FPU/ml.

Analysis:

A Waters High Performance Liquid Chromatography (HPLC) with Aminex HPX 87 P BioRad Column and de-ashing guard column was used to perform the analysis. The analysis was performed in our lab as well as at Michigan Biotechnology International (MBI), East Lansing, Mich.

In the optimized AFEX pretreatment conditions of 1 kg $NH_3$:1 kg DBM, 60% MC, 90° C. ideally, there is 90% glucose and 70% xylose conversion. If the decrease in the amount of ammonia used under nitrogen pressure is back calculated, there is a 1.5, 2 and 5 fold increase in yield under nitrogen pressure proportional to the ammonia loadings of 0.5, 0.3 and 0.1 kg $NH_3$: Kg DBM, respectively. In other words, there is a 5 fold savings on the amount of ammonia when AFEX under nitrogen pressure is employed at 0.1:1 ammonia charge compared to 1:1. The amount of ammonia has decreased 10 times (1:1 to 0.1:10 while both the glucose and xylose yields has dropped to ½ from 90% to 45% and 70% to 35% for glucose and xylose, respectively. The results are shown in FIGS. 3 to 9.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A process for the treatment of a plant biomass, the process comprising:
   (a) performing an ammonia treatment process comprising:
      (i) contacting a lignocellulosic plant biomass, which has been ground and which contains varying moisture contents, with a source of ammonia comprising at least one of anhydrous ammonia in the liquid state, anhydrous ammonia in the vapor state, a concentrated ammonia:water mixture in the liquid state, and a concentrated ammonia:water mixture in the vapor state, thereby forming a mixture in which the ratio of ammonia (as $NH_3$) to dry plant biomass is between about 0.1:1 and 0.75:1 and the ratio of water to dry plant biomass is between about 0.2:1 and 1.5:1;
      (ii) maintaining the mixture in a closed vessel at temperatures between about 50° C. and 140° C. for a period of time;
      (iii) maintaining the ammonia in contact with the lignocellulosic plant biomass and increasing an amount of the ammonia in the liquid state by managing a headspace volume of the closed vessel; and
      (iv) rapidly releasing pressure from the vessel by releasing ammonia from the vessel to form a treated biomass, the treated biomass having an increased reactivity of plant polymers comprising hemicellulose and cellulose; and
   (b) removing the treated plant biomass which has increased reactivity from the vessel.

2. The process of claim 1, further comprising:
   (c) extracting the treated plant biomass from step (b) to remove lignin and other compounds that can interfere with the ability of enzymes to hydrolyze the treated biomass.

3. The process of claim 1 wherein managing the headspace volume in step (a) comprises compressing by a mechanical means the headspace volume inside the closed vessel and thereby increasing the fraction of the total ammonia that is in the liquid phase.

4. The process of claim 1 wherein managing the headspace volume in step (a) comprises introducing nitrogen under pressure into a the headspace volume of the vessel so as to increase the fraction of the total ammonia that is in the liquid phase.

5. The process of claim 1 wherein managing the headspace volume in step (a) comprises introducing particles of an inert solid material into the vessel so as to increase the fraction of the total ammonia that is in the liquid phase.

6. The process of claim 1 wherein managing the headspace volume in step (a) comprises introducing particles of a solid material selected from the group consisting of sand and iron filings into the vessel so as to increase the fraction of the total ammonia that is in the liquid phase.

7. The process of claim 1 wherein managing the headspace volume in step (a) comprises connecting the a headspace volume of the closed vessel is-connected with a headspace volume of an appropriate ammonia storage vessel so as to increase the fraction of the total ammonia that is in the liquid phase in the closed vessel.

8. The process of claim 1 wherein the ratio of ammonia to dry plant biomass is between about 0.1:1 and 0.5:1.

9. The process of claim 1 wherein the ratio of ammonia to dry plant biomass is between about 0.1:1 and 0.3:1.

10. A process for the treatment of a plant biomass, the process comprising:
    (a) performing an ammonia treatment process comprising:
       (i) contacting a lignocellulosic plant biomass, which has been ground and which contains varying moisture contents, with a source of ammonia comprising at least one of anhydrous ammonia in the liquid state, anhydrous ammonia in the vapor state, a concentrated ammonia:water mixture in the liquid state, and a concentrated ammonia:water mixture in the vapor state, thereby forming a mixture in which the ratio of ammonia (as $NH_3$) to dry plant biomass is between about 0.1:1 and 1.2:1 and the ratio of water to dry plant biomass is between about 0.2:1 and 1.5:1;
       (ii) maintaining the mixture in a closed vessel at temperatures between about 50° C. and 140° C. for a period of time;
       (iii) introducing nitrogen under pressure into a headspace volume of the vessel to increase the fraction of the total ammonia that is in the liquid phase in the closed vessel and in contact with the lignocellulosic plant biomass; and
       (iv) rapidly releasing pressure from the vessel by releasing ammonia from the vessel to form a treated biomass, the treated biomass having an increased reactivity of plant polymers comprising hemicellulose and cellulose; and
    (b) removing the treated plant biomass which has increased reactivity from the vessel.

11. The process of claim 10, further comprising:
    (c) extracting the treated plant biomass from step (b) to remove lignin and other compounds that can interfere with the ability of enzymes to hydrolyze the treated biomass.

12. The process of claim 10 wherein the ratio of ammonia to dry plant biomass is between about 0.2:1 and 1.2:1.

13. The process of claim 10 wherein the ratio of ammonia to dry plant biomass is between about 0.1:1 and 1:1.

14. The process of claim 10 wherein the ratio of ammonia to dry plant biomass is between about 0.1:1 and 0.5:1.

15. The process of claim 10 wherein the ratio of ammonia to dry plant biomass is between about 0.1:1 and 0.3:1.

* * * * *

UNITED STATES PATENT AND TRADEMARK OFFICE
CERTIFICATE OF CORRECTION

| | | |
|---|---|---|
| PATENT NO. | : 7,915,017 B2 | Page 1 of 1 |
| APPLICATION NO. | : 11/901336 | |
| DATED | : March 29, 2011 | |
| INVENTOR(S) | : Bruce Dale et al. | |

It is certified that error appears in the above-identified patent and that said Letters Patent is hereby corrected as shown below:

On the face page, in field (56), under "Other Publications", in column 2, line 2, delete "availabiltiy" and insert -- availability --, therefor.

In column 14, line 3, in Claim 4, after "into" delete "a".

In column 14, line 15, in Claim 7, after "the" delete "a".

In column 14, line 16, in Claim 7, after "vessel" delete "is-connected".

Signed and Sealed this
Eighth Day of November, 2011

David J. Kappos
*Director of the United States Patent and Trademark Office*

UNITED STATES PATENT AND TRADEMARK OFFICE
CERTIFICATE OF CORRECTION

PATENT NO. : 7,915,017 B2  
APPLICATION NO. : 11/901336  
DATED : March 29, 2011  
INVENTOR(S) : Bruce Dale

Page 1 of 1

It is certified that error appears in the above-identified patent and that said Letters Patent is hereby corrected as shown below:

In the Specification

Col 1/Line 21: Error reads as "Not Applicable." and should read as "This invention was made with government support under XCO-3-33033-01 awarded by the U.S. Department of Energy and under 00-52104-9663 awarded by the U.S. Department of Agriculture. The government has certain rights in the invention."

Signed and Sealed this  
Nineteenth Day of August, 2014

Michelle K. Lee  
*Deputy Director of the United States Patent and Trademark Office*